US 6,558,313 B1

(12) United States Patent  
Knighton et al.

(10) Patent No.: US 6,558,313 B1
(45) Date of Patent: May 6, 2003

(54) VEIN HARVESTING SYSTEM AND METHOD

(75) Inventors: David R. Knighton, Minneapolis, MN (US); Vance D. Fiegel, New Brighton, MN (US)

(73) Assignee: Embro Corporation, St. Louis Park, MN (US)

( * ) Notice: Subject to any disclaimer, the term of this patent is extended or adjusted under 35 U.S.C. 154(b) by 160 days.

(21) Appl. No.: 09/715,382

(22) Filed: Nov. 17, 2000

(51) Int. Cl.⁷ ................................................. A61F 2/04
(52) U.S. Cl. ......................................................... 600/36
(58) Field of Search ............................ 600/36, 213, 212, 600/210, 235, 245, 246; 604/103.01; 606/159, 170, 190, 15, 2

(56) References Cited

U.S. PATENT DOCUMENTS

| 1,867,624 A | 7/1932 | Hoffman |
| 2,001,169 A | 5/1935 | Wallace |
| 2,011,169 A | 8/1935 | Wappler |
| 2,028,635 A | 1/1936 | Wappler |
| 2,316,297 A | 4/1943 | Southerland et al. |
| 2,868,206 A | 1/1959 | Stoesser |
| 2,944,552 A | 7/1960 | Cannon |
| 3,185,155 A | 5/1965 | Slaten et al. |
| 3,336,916 A | 8/1967 | Edlich |
| 3,856,016 A | 12/1974 | Davis |
| 3,882,854 A | 5/1975 | Hulka et al. |
| 3,934,115 A | 1/1976 | Peterson |
| 4,038,987 A | 8/1977 | Komiya |
| 4,362,160 A | 12/1982 | Hiltebrandt |
| 4,440,170 A | 4/1984 | Golden et al. |
| 4,556,058 A | 12/1985 | Green |
| 4,768,508 A | 9/1988 | Chin et al. |
| 4,793,346 A | 12/1988 | Mindich |
| 5,037,433 A | 8/1991 | Wilk et al. |
| 5,284,478 A | 2/1994 | Nobles et al. |
| 5,425,355 A | 6/1995 | Kulick |
| 5,447,513 A | 9/1995 | Davison et al. |
| 5,549,637 A | 8/1996 | Crainich |
| 5,772,576 A | 6/1998 | Knighton et al. |
| 5,782,753 A | 7/1998 | DeFonzo et al. |
| 5,795,331 A | 8/1998 | Cragg et al. |
| RE36,043 E | 1/1999 | Knighton |
| 6,071,232 A | 6/2000 | Knighton et al. |
| 6,113,588 A | 9/2000 | Duhaylongsod et al. |
| 6,193,653 B1 | 2/2001 | Evans et al. |
| 6,196,968 B1 | 3/2001 | Rydin et al. |
| 6,228,025 B1 | 5/2001 | Hipps et al. |
| 6,322,499 B1 | 11/2001 | Evans et al. |
| 6,350,236 B1 | 2/2002 | Hipps et al. |

FOREIGN PATENT DOCUMENTS

| DE | 39 42 589 A1 | 7/1991 |
| GB | 2 082 459 A | 3/1982 |
| GB | 2 195 540 A | 4/1988 |
| SU | 112367 | 7/1957 |
| SU | 510235 | 5/1976 |
| SU | 1371689 A1 | 3/1986 |

OTHER PUBLICATIONS

PCT Search Report for corresponding PCT/US01/45166 (4 pages).

(List continued on next page.)

Primary Examiner—Teresa Walberg
Assistant Examiner—Fadi H. Dahbour
(74) Attorney, Agent, or Firm—Popovich & Wiles, P.A.

(57) ABSTRACT

A system and a method for harvesting a section of a blood vessel from a patient's body for further use. The system includes an expandable hood that creates a workspace for the dissection and removal of the vessel and a telescoping device that has tools at its distal end. The blood vessel is cut at a distal location and a light catheter inserted to illuminate the area of dissection. The system can remove a section of the saphenous vein for use in coronary bypass surgery.

11 Claims, 5 Drawing Sheets

OTHER PUBLICATIONS

DeLaria et al., "Leg Wound Complications Associated with Coronary Revascularization," *J. Thorac. Cardiovasc. Surg.*, 81:403–407 (1981).

Dimitri et al., "A Quick and Atraumatic Method of Autologous Vein Harvesting Using the Subcutaneous Extraluminal Dissector," *J. Cardiovasc. Surg.*, 28:103–111 (1987).

Hauer et al., "Endoscopic Subfacial Discission of Perforating Veins," *Surgical Endosc.*, 2:5–12 (1988).

"Incision Decision", Atrium Medical Corporation advertisement, appearing in *J. Thorac. Cardiovasc. Surg.*, 83(4) (1982).

Meldrum–Hanna et al., "Long Saphaneous Vein Harvesting," *J. Surg.*, 56:923–924 (1986).

Moazami et al., "Minimally Invasive Greater Saphenous Vein Harvesting for Coronary Artery Bypass Surgery," *Surgical Rounds*, pp. 94–98 (Mar. 1997).

Rashid et al., "Subcutaneous Technique for Saphenous Vein Harvest," *Ann. Thorac. Surg.*, 37(2):169–170 (1984).

"Saphenous Vein Grafts are No. 1. Period. ," Atrium Medical Corporation advertisement, appearing in *J. Thorac. Cardiovasc. Surg.*, 81(6) (1981).

Wheatley, D.J., ed., *Surgery of Coronary Artery Disease*, C.V. Mosby Co., pp. 348–349, 374–375.

Commonly assigned, co–pending U.S. Ser. No. 09/715,665, filed Nov. 17, 2000.

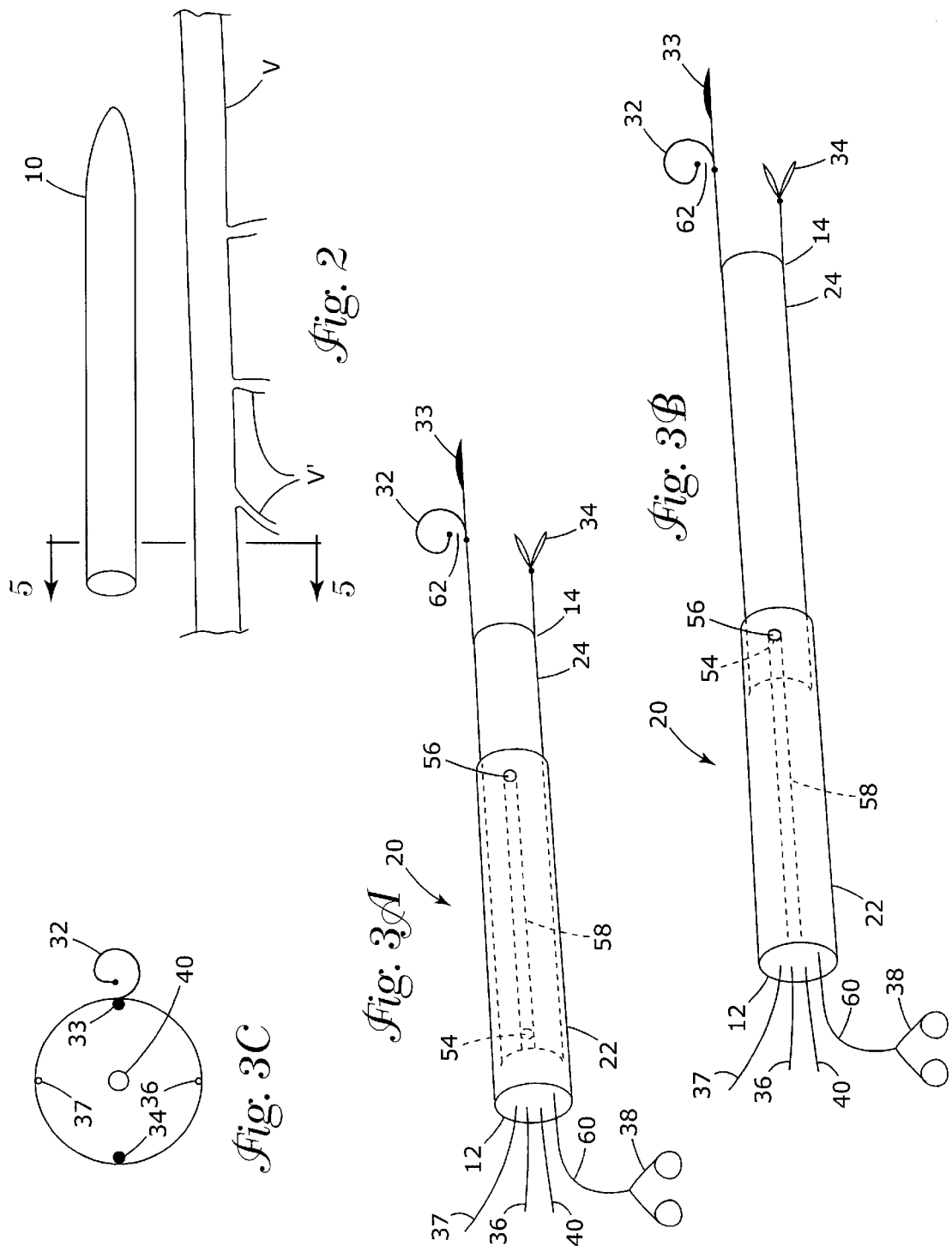

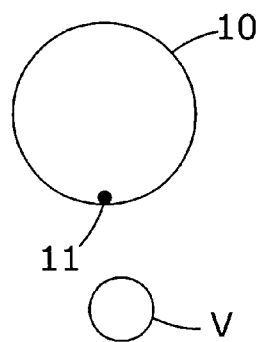
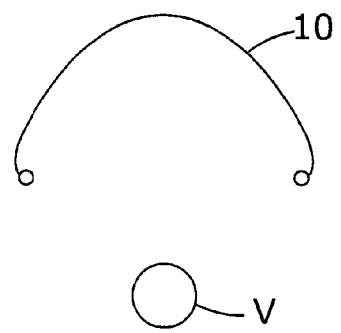
Fig. 5A                Fig. 5B
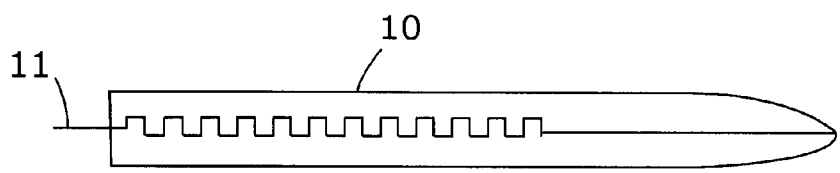
Fig. 5C

VEIN HARVESTING SYSTEM AND METHOD

FIELD OF THE INVENTION

This invention relates to a system and a method for harvesting a generally cylindrical tissue structure from the body of a patient. More particularly, the invention is directed to a system and a method for harvesting a section of a blood vessel from a patient.

BACKGROUND OF THE INVENTION

In certain circumstances it is desirable to remove sections of tubular tissue structure from a patient's body. Such tissue may be used in another part of the patient's body, may be transplanted into a second patient's body or may be discarded. As used herein, the term "tubular tissue structure" includes blood vessels, tendons, bile ducts, nerves and any other similar tissue formation which is generally tubular in structure and capable of being separated from surrounding tissue. Although the invention herein will be discussed in terms of harvesting blood vessels it should be understood that the apparatus and method described are equally applicable to harvesting other solid or cylindrical tubular tissue structure.

Vein harvesting is commonly done in connection with coronary artery bypass surgery. The saphenous vein is a subcutaneous vein which is often used for coronary artery bypass grafting, infra-inguinal bypass grafting and vein-vein bypass grafting. Other vessels may also be used including the internal mammary artery, the radial artery, and/or the lesser saphenous vein. Previously, it has been necessary to make an incision along the full length of the vein section to be removed. The vein is then freed by severing and ligating the branches of the vein, after which the section of the vein can be removed from the patient. The full-length incision must then be closed, for example by suturing or stapling. Obviously, the harvesting of the vein in this manner leaves disfiguring scars which are cosmetically undesirable. Additionally, the large incision creates a risk of infection to the patient and may not heal properly, especially with those patients who have poor circulation in their extremities. Such an incision may create a chronic non-healing wound, requiring significant and costly medical treatment.

Devices for harvesting a section of a blood vessel without creating a full-length incision have been suggested and include that described in U.S. Pat. No. 4,793,346 (Mindich) and UK Patent No. GB 20 82 459A. These patents describe methods that use incisions at either end of the blood vessel to be harvested. Such devices and methods can be disadvantageous because greater blood loss than is necessary can result. These devices may also remove more tissue than is necessary because the size of the cutting device is not readily adaptable to the changes in the size of the blood vessel. In addition, these patents describe techniques which have a high probability of damaging the vessel, making it unsuitable for use as a vascular conduit.

In U.S. Pat. No. RE 36,043 (Knighton), a device and a method for vein removal are disclosed which solve some of the problems associated with the use of prior art devices. Knighton discloses an endoscope having a lumen extending longitudinally through the scope body. The endoscope includes means for viewing an area adjacent the distal end of the lumen. The lumen has a lateral dimension large enough to accommodate the blood vessel being harvested and at least one tool for use in harvesting the blood vessel. A first end of the blood vessel section to be harvested is exposed through an incision in the patient's body. A dissecting tool and a gripping tool are inserted through the lumen of the endoscope and used to dissect the blood vessel away from the surrounding connective tissue of the patient's body. Additional tools are provided for use through the lumen of the endoscope to remove body fluids and coagulate bleeding tissue, to ligate and sever side branches from the blood vessel to be harvested, and to ligate and sever a distal end of the blood vessel to be harvested when a desired length of blood vessel has been dissected. Only a small incision in the patient's body is necessary to harvest a relatively long length of blood vessel in a precise and controlled manner using this device and procedure.

U.S. Pat. No. 5,772,576 (Knighton et al.) also describes a device and method for vein removal. The device has one or more lumens extending through a body portion. One lumen is sized to accommodate a blood vessel and at least one tool for use in removing the vessel. The device may also include viewing means so that the operator may remotely view an area adjacent the distal end of the body portion. The device protects the vessel being removed from damage by the tools used in the procedure, which is critical since the blood vessel is destined for reuse (as in arterial bypass). In addition, a single operator can use the device.

In commonly assigned, co-pending application Ser. No. 09/715,665, filed on even date herewith, entitled "Vein Harvesting System and Method", the entirety of which is incorporated herein by reference, a system that is easier to use and minimizes damage to a blood vessel is described. In this system, a multi-lumen tube is used in conjunction with a housing having a removable lower portion. The housing provides a workspace for the removal of a blood vessel and the multi-lumen tube and associated tools provide a means to see and to remove a desired length of vein and cut and cauterize any vein side branches while minimizing damage to the vein and trauma to the patient. An additional problem with present technology is determining the course of the main saphenous trunk versus a large side branch. The course of the main vein would also be beneficial to see well ahead of the dissection to facilitate the speed of dissection.

The need also exists for a vein harvester having a variable length and further having tools that would be easier and more convenient to use. The tools typically used in the current procedures tend to be long and difficult to control. Having tools with a variable length would allow for an easier, more precise, and more rapid procedure.

SUMMARY OF THE INVENTION

This invention is a system and a method for the harvesting of a blood vessel. The system comprises an expandable hood to make a workspace for extraction of the vein and an extendible or telescoping device having desired tools at its distal end. The tools are activated at the proximal end of the telescoping device. The method comprises illuminating the dissection area via a light catheter that is inside the lumen of the blood vessel and deploying the telescoping device to the length desired to dissect the vein from surrounding tissue.

In a first aspect the invention is a method of harvesting a section of a vessel from a human or animal body. The method comprises exposing the vessel section to be harvested through an incision in the body; providing a light source; placing the light source in the lumen of the vessel, the light source being sufficient to illuminate substantially the entire vessel section and vessel side branches extending from the vessel section with an intensity which is visible from an exterior of the vessel section; dissecting the vessel away from surrounding connective tissue of the body with a dissecting tool inserted through the incision; viewing the dissection of the vessel with a viewing element inserted through the incision; cutting the vessel at proximal and distal ends of the vessel section; and removing the vessel section from the patient's body. The vessel section may be exposed through first and second incisions with the dissecting tool and viewing element inserted through the first incision and the light source placed in the vessel lumen through the second incision. The first incision may be made over a proximal end of the vessel section and the second incision over a distal end of the vessel section. The method may further comprise providing a telescoping member having first and second substantially cylindrical segments, the second segment sized to fit within a lumen of the first segment, the telescoping member being adjustable in length from a fully collapsed position where the second segment is contained substantially within the first segment to a fully extended position where the second segment is substantially removed from the first segment, the telescoping member having the dissecting tool connected to a distal end of the second segment, and inserting the telescoping member through the incision. The step of proving the telescoping member may comprise providing a telescoping member wherein the viewing element and tool used to cut the vessel are connected to the distal end of the second segment. The method may comprise providing a hood member configured to be moveable from a first closed position to a second open position; inserting the hood member through the incision, adjacent the vessel; and creating a working space adjacent the vessel by opening the hood member from the first closed position to the second open position.

In another aspect the invention is a system for harvesting a section of a vessel from an incision in a human or animal body. The system comprises a light source sized and configured to be inserted into a lumen of the vessel, the light source being sufficient to illuminate substantially the entire vessel section with an intensity which is visible from an exterior of the vessel section; a viewing element configured to be insertable through the incision and capable of viewing the illuminated vessel section; and at least on tool used to harvest the vessel section, the at least one tool being sized to be inserted through the incision. This system may include a telescoping member having first and second substantially cylindrical segments, the second segment sized to fit within a lumen of the first segment, the telescoping member being adjustable in length from a fully collapsed position to a fully extended position by slidably adjusting the extent to which the second segment is contained in the lumen of the first segment, the telescoping element having a dissecting tool connected thereto. The viewing element may be connected to the telescoping member. A dissection element connected to the telescoping member may also be included. A hood member configured to be moveable from a first closed position to a second open position may be included in the system. The hood member is sized to be inserted through the incision in the closed position and placed adjacent the vessel section. The hood is further configured to create a working space adjacent the vessel when moved to the open position.

BRIEF DESCRIPTION OF THE DRAWINGS

FIG. 2 is a perspective view of the expandable hood in its retracted position over the vein to be harvested.

FIG. 3A is a perspective view of the telescoping device of the present invention in its retracted position.

FIG. 3B is a perspective view of the telescoping device of the present invention in its fully extended position.

FIG. 3C is an exploded view of the distal end of the telescoping device of FIGS. 3A and 3B.

FIG. 5A is a sectional view along line 5—5 of FIG. 2.

FIG. 5B is a view similar to FIG. 5A but with expandable hood in its filly expanded position.

FIG. 5C is a bottom view of the expandable hood.

DETAILED DESCRIPTION OF THE PREFERRED EMBODIMENTS

The present invention is a system and a method for harvesting a tubular tissue section such as a section of a vessel from a patient's body for use in another part of a patient's body or for transplanting into a second patient's body. For example, a section of the saphenous vein may be removed for use in coronary bypass surgery. The saphenous vein travels along the medial side of the foot, leg, and thigh, where it joins with the femoral vein near the groin. Although specific reference herein is made to harvesting a section of saphenous vein it should be understood that the invention could be used to harvest other tubular tissue sections from human or animal bodies.

The terms "distal" and "proximal" as used herein refer to the method of use of the system. "Proximal" refers to a location closer to the physician and "distal" refers to a location farther from the physician. "Upper" and "lower" also are terms that refer to an orientation with respect to the use of the device, that is, relative to the physician.

In the method of this invention, the patient is first prepared for removal of the vein. The method is suitable for removal of any vein or tubular tissue structure; however, the invention is exemplified by reference to the saphenous vein. A first incision is made in the area from which the vein is to be harvested. For example, the incision is made in the groin area for harvesting the saphenous vein. A second, distal, incision is also made. For example, this distal incision will be near the knee (either above or below the joint) if the longest section possible of vein is needed. An expandable hood is inserted through the first incision and positioned over the top of the saphenous vein. This serves to lift surrounding tissue away from the vein. Then the expandable hood is expanded to create a space sufficient to permit the use of tools so that the vein may be dissected.

At the site of the distal incision, the vein or a side branch is cut and a light catheter (e.g., a fiber optic cable) is inserted into the lumen of the vein to illuminate the area of dissection and display the lumen of the vein. A device that is extendible, referred to as a telescoping device, is provided with tools at its distal end and is inserted through the first incision and under the expandable hood. The telescoping device provides the means to dissect the vein from the connective tissue and to cut and clip or cauterize any vein side branches. The telescopic device has a viewing fiber optic cable connected to a monitor so that the physician can see the dissection area. In addition, suction may be provided to remove blood and debris from the dissection field. Irrigation of the area of the vein with saline also may be provided through the telescoping device.

Figure 1:
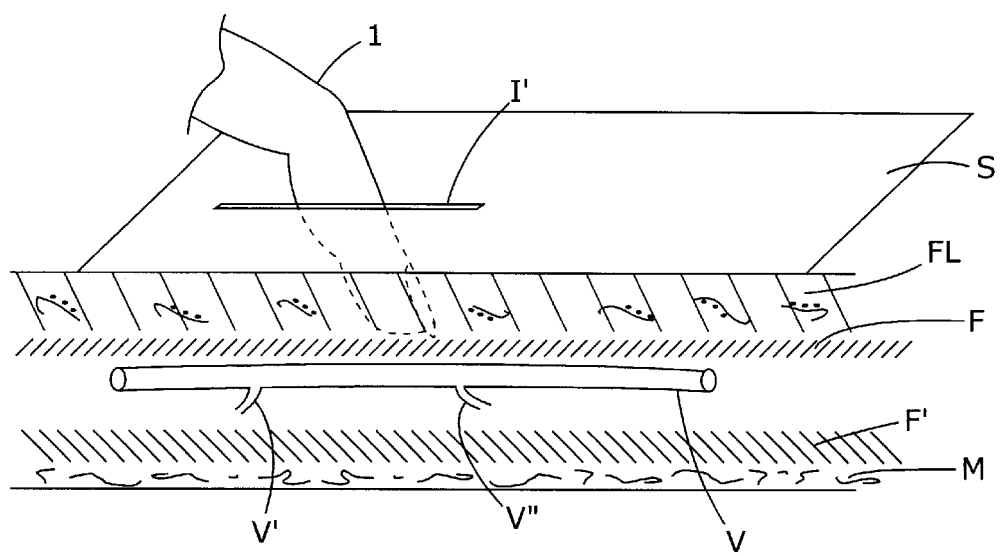
FIG. 1 is a partial cross-sectional view of a portion of a patient's body prepared for insertion of the device of the invention.

Turning now to the Figures, the system and method of the invention are illustrated. After proper preparation of the incision site, the physician makes a small incision I' (e.g., about 3 cm long) over the proximal aspect of the blood vessel to be harvested. FIG. 1 illustrates that incision I' is made in the region above the saphenous vein V. Vein V typically has side branches V'. The incision is made in the skin (S) and through various layers such as scarpa's fascia (F) and subcutaneous fat layer (FL). Underneath the saphenous vein is fascia (F') and muscle (M). For the sake of simplicity, such layers are not shown in FIGS. 2, 3A, 3B, 5A, 5B, and 6.

As shown in FIG. 1 the physician inserts a finger identified as reference numeral 1 to separate the various tissue layers from the saphenous vein and to make sufficient room to insert expandable hood 10 into incision I'. Hood 10 is inserted into the incision and moved distally a desired length of the saphenous vein. Optionally, a blunt dissector could be used to initially open a small space to allow for easier insertion of the hood. FIG. 5A is a cross-sectional view along line 5—5 in FIG. 2. In this position a portion of the proximal end of hood 10 extends from the incision. Hood 10 is now in a first closed or contracted position. Then hood 10 is expanded, or opened, as shown in cross-section in FIG. 5B. Hood 10 is opened to a second expanded position by removing pin 11 from the proximal end of the hood. The physician does this by simply grabbing and pulling on a proximal portion of the pin which extends from the hood. The hood is comprised of metal or plastic which is biased in the open or expanded direction. The pin 11 extends through holes in teeth 50 and 52 located on first and second lateral edges of the hood. As best seen in FIG. 5C in the closed position the teeth 50 and 52 mesh and are held together by the pin so that the hood remains in the closed position. Removal of pin 11 releases the lateral edges allowing the hood to expand to its open or expanded position. The movement of the hood from the closed to open position creates a sufficient working space above the saphenous vein for tools used in the harvesting procedure. Once the hood is expanded the site is ready to receive telescoping device 20.

Telescoping device 20 has proximal end 12 and distal end 14 and is constructed of a rigid material such as metal or plastic. Device 20 is shown in FIGS. 3A and 3B as having two telescoping segments, 22 and 24. It is to be understood that more telescoping segments could be used in the system of this invention depending on the length and degree of articulation desired. The length of one segment is shown as being about the same as the length of another segment, although it is also to be understood that the segments may have lengths different from one another.

Device 20 is advanced along the top of the saphenous vein under expandable hood 10 by extending the telescoping segments. FIG. 3A shows the device in a collapsed or non-extended condition with a substantial portion of segment 24 lying within segment 22. Segment 24 is sized to be friction fit within segment 22. The vein harvesting procedure is usually begun with the device in the collapsed position. As additional length is desired the device is withdrawn from the incision far enough so that the physician can grasp the two (or more) sections and pull them apart. The physician may adjust the relative position of the segments until the device has a desired length. The segments are friction fit in a manner that maintains the desired position between segments so that the device can continue to be used to dissect the vessel without axial slippage of the sections relative to one another. It will be appreciated that other means of extending the telescoping sections could be used such as using a worm gear and stepper motor. The segments are extended as the vein is dissected to the desired length, which is dependent upon the length of the vein to be dissected. As best seen in FIGS. 3A and 3B a spring-loaded dimple 54 on the proximal portion of segment 24 mates with a hole 56 in the distal portion of segment 22 to act as a positive stop of the relative movement between the sections. Alignment of dimple 54 with hole 56 may be accomplished by providing a longitudinal groove 58 on the inner surface of segment 22 in which dimple 54 is positioned. The longitudinal groove maintains the axial alignment of the segments as the device is extended. It will be apparent to those of skill in the art that other means of limiting the axial movement of the segments with respect to one another could be provided.

In FIG. 3A the device is shown in the collapsed position while in 3B the device is shown in the fully extended position. FIG. 3C shows a distal end view of the device and the various tools and viewing means connected thereto. Associated with telescoping device 20 are appropriate tools at distal end 14 which include vein dissector 32 and cutting means, such as bipolar scissors 34. Inserted through proximal end 12 is suction line 36, which is contained within central lumens of segments 22 and 24 and which provides a means to remove blood, debris, and irrigation fluid such as saline from the surgical area. Actuator 38 is operably connected through flexible line 60 to the bipolar scissors 34 and permits their operation at the desired time. Fiber optic line 40 is provided to detect the light provided by the light catheter in the vein. The fiber optic line is connected to a monitor (not shown) so that the physician can see the dissection area. An irrigation line 37 is provided and connected to an irrigation source (not shown) at one end and to the distal end of the telescoping device at the other. Lines 36, 37, 40, and 60 extend from the proximal end of the device and are contained within the lumens of segments 22 and 24. Lines 36, 37, 40, and 60 are connected at the distal end of segment 22.

Vein dissector 32 is fixed at the end of segment 22, preferably at a circumferential position spaced approximately 180° from the position at which line 60 and bipolar scissors 34 are fixed. The vein dissector 32 is provided with an open loop having an opening 62 so that it can be slipped onto and off of the vein as desired. For example, during dissection of the vein if a side branch is encountered the vein dissector can be removed and the device rotated 180° so that the bipolar scissors can be used to cut and coagulate the side branch. The device is then rotated back and the vein dissector slipped over the vein and advanced in the distal direction so the dissection process is continued. Although a spacing of 180° is preferred between the vein dissector and bipolar scissors it will be appreciated that other spacing could be used so long as the spacing is sufficient to allow the tools to be used without interference from one another. Vein dissector 32 includes a blunt tip portion 33 which is used as an additional means of dissecting tissue from the vein and as a probe. This vein dissector may be a full circular dissector or, more preferably, a loop dissector as shown, which permits the vein to be dissected and removed from the dissector any time it is desired.

Cutting means 34 preferably is a bipolar scissors. Such scissors are configured to cut and cauterize size branches V' of the vein as they are encountered during the dissection of vein V. Alternatively, any cutting means can be used and appropriate ligation means (such as a suture or a clip) also can be used.

The actuator is adapted to operate cutting means 34, preferably bipolar scissors, which cuts and cauterizes side branches V' of vein V as the dissection proceeds. The dissection process proceeds distally along blood vessel V. The operator of the device views the dissection process (occurring at the area immediately adjacent distal end 14 of telescoping device 20) through the optical viewing device/detector 40 and associated monitor. Optionally, a saline infusion line 37 may be included to ensure that the lens at the distal end of the fiber optic line remains clear.

Figure 4A:
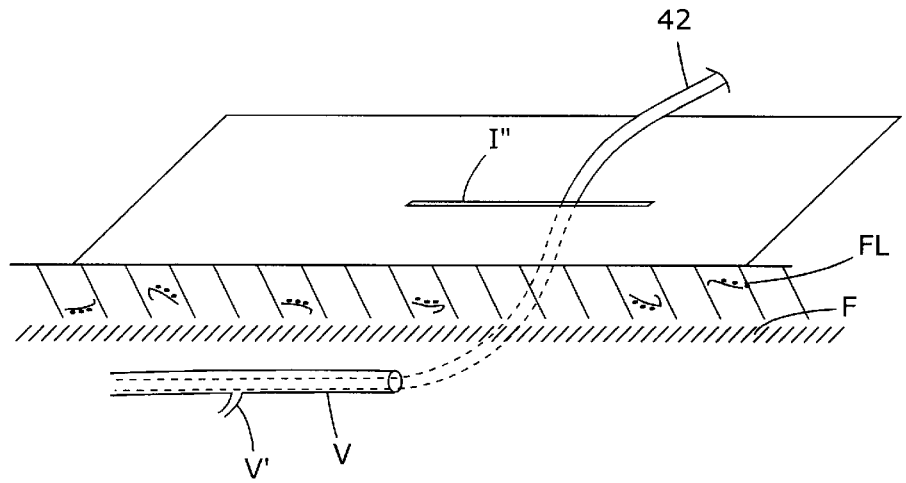
FIG. 4A is a partial cross-sectional view of a portion of a patient's body illustrating insertion of the light catheter into the vein to be harvested.
Figure 4B:
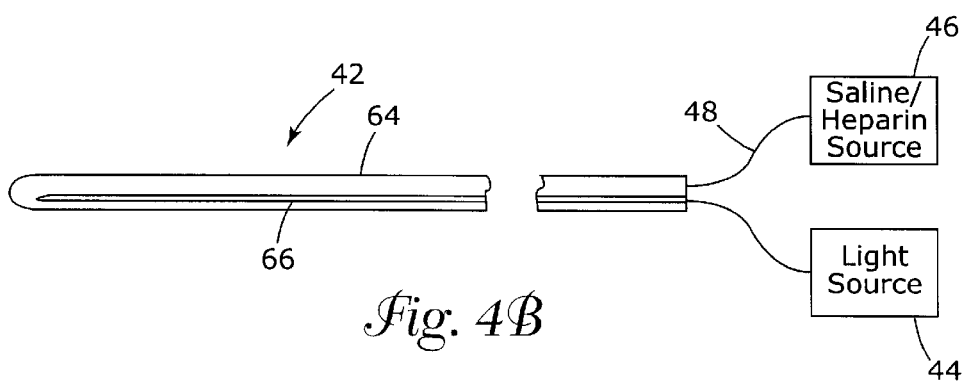
FIG. 4B is a partial plan view of the light catheter of the present invention.

As seen in FIGS. 4A and 4B light catheter 42 is inserted via distal incision I" into the saphenous vein at the distal end. Alternatively catheter 42 may be inserted into a large side branch located near the distal end of the vein. Light catheter 42 is moved proximally to the proximal end of the vein in the direction of incision I'. The construction of catheter 42 is best seen in FIG. 4B which is a partial view of catheter 42. Catheter 42 includes a transparent outer sheath 64 comprised of a material capable of transmitting light along the entire length of the catheter. A fiber optic cable 66 is connected to a light source 44. The catheter is constructed so that when inserted into a vein it will light up substantially the entire vein section and side branches along the length of the catheter. It should be understood that any light source sufficient to illuminate light catheter 42 along its length would be suitable for use in this invention. For example, light transmissive fluid or an internal chemical light source could be used. A heparin and/or saline source 46 is connected to the lumen of catheter 42 via line 48. Holes 68 are provided in catheter 42 so that heparin and/or saline can be injected into the vein.

During a typical saphenous vein harvesting procedure the vein harvesting system is used as follows. A first incision I' is made over the groin area. A second distal incision I" is made above or below the knee depending on the length of vein needed. Expandable hood 10 is inserted into incision I' over the saphenous vein. The hood is expanded to create sufficient space to use the telescoping device including its dissecting and cutting tools. At the second incision the saphenous vein or a side branch is cut and light catheter 42 is inserted into the saphenous vein. Light catheter 42 is advanced in the proximal direction to a position sufficient to light the saphenous vein and side branches between the area of the first and second incisions. The telescoping device 20 is inserted beneath the hood through the first incision after the physician has exposed the saphenous vein with his or her finger. The saphenous vein is inserted into the vein dissector 32 through slot 62. The procedure is usually started with the telescoping device fully collapsed although the segments may be manipulated to lengthen the device if desired.

Figure 6:
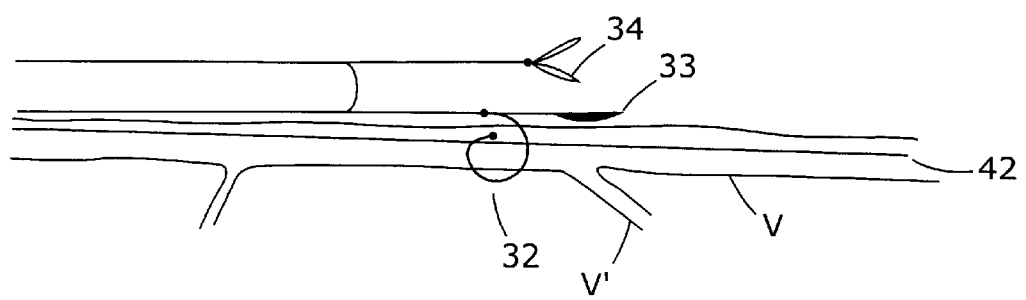
FIG. 6 is a partial view of the dissection process showing telescoping device used to dissect vein V and light catheter in the lumen of vein V.

The device is advanced under direct vision of the physician until no longer visible by eye, after which the physician views the process on the monitor. By utilizing light catheter 42 the physician's view of the dissection and cutting process is improved over prior art procedures where the light source is external to the vein. FIG. 6 shows the use of the telescoping device during the dissection of a vein containing the light catheter.

When a side branch is encountered the vein dissector is removed from the vein and the telescoping device rotated so that the bipolar scissors (or other cutting means) can be used to cut and coagulate (or clip) the side branch. The device is then rotated and the vein dissector slipped over the vein so the dissection process can continue.

When the telescoping device has been inserted to a distance where it becomes necessary to lengthen the device to continue the dissection the physician withdraws the device through the incision far enough so that the sections can be grasped and pulled apart to lengthen the device a desired amount. The device is then moved distally and the dissection process continued.

When a sufficient length of the vein has been dissected the device is removed from the first incision and the vein is cut at the location of the first and second incisions and then removed, usually from the first incision.

It should be appreciated that the light catheter could be inserted through the same incision as the telescoping device and inserted into the vessel through a side branch.

Although particular embodiments have been disclosed herein in detail, this has been done for purposes of illustration only, and is not intended to be limiting with respect to the scope of the claims. In particular, it is contemplated that various substitutions, alterations, and modifications may be made to the invention without departing from the spirit and scope of the invention as defined by the claims. In addition, it should be understood that although the various components and tools of this invention have been disclosed as a system it is possible and advantageous to use them separately. For example, the expandable hood of this invention could be used advantageously with known vein harvesting tools to create working space therefore. The telescoping device could be used without the expandable hood and could be used without the light catheter if provided with a light source. Further, the light catheter could advantageously be used to improve the use of prior art vein harvesting tools and techniques, the effectiveness of which would be enhanced by more clearly being able to visualize the vessel and side branches.

What is claimed is:

1. A method of harvesting a section of a vessel from a human or animal body comprising:

exposing the vessel section to be harvested through first and second incisions in the body;

providing a light source;

placing the light source through the second incision into the lumen of the vessel, the light source being sufficient to illuminate substantially the entire vessel section and vessel side branches extending from the vessel section with an intensity which is visible from an exterior of the vessel section;

dissecting the vessel away from surrounding connective tissue of the body with a dissecting tool inserted through the first incision;

viewing the dissection of the vessel with a viewing element inserted through the first incision;

cutting the vessel at proximal and distal ends of the vessel section; and removing the vessel section from the patient's body.

2. The method of claim 1 wherein the first incision is made over a proximal end of the vessel section and the second incision is made over a distal end of the vessel section.

3. The method of claim 1 further comprising:

providing a hood member configured to be moveable from a first closed position to a second open position;

inserting the hood member through the first incision, adjacent the vessel; and creating a working space adjacent the vessel by opening the hood member from the first closed position to the second open position.

4. A method of harvesting a section of a vessel from a human or animal body comprising:

exposing the vessel section to be harvested through an incision in the body;

providing a light source;

placing the light source in the lumen of the vessel, the light source being sufficient to illuminate substantially the entire vessel section and vessel side branches extending from the vessel section with an intensity which is visible from an exterior of the vessel section;

dissecting the vessel away from surrounding connective tissue of the body with a dissecting tool inserted through the incision;

viewing the dissection of the vessel with a viewing element inserted through the incision;

cutting the vessel at proximal and distal ends of the vessel section;

removing the vessel section from the patient's body;

providing a telescoping member having first and second substantially cylindrical segments, the second segment sized to fit within a lumen of the first segment, the telescoping member being adjustable in length from a fully collapsed position where the second segment is contained substantially within the first segment to a fully extended position where the second segment is substantially removed from the first segment, the telescoping member having the dissecting tool connected to a distal end of the second segment; and inserting the telescoping member through the incision.

5. The method of claim 4 wherein the step of proving the telescoping member comprises providing a telescoping member wherein the viewing element and tool used to cut the vessel are connected to the distal end of the second segment.

6. The method of claim 4 further comprising:

providing a hood member configured to be moveable from a first closed position to a second open position;

inserting the hood member through the incision, adjacent the vessel; and creating a working space adjacent the vessel by opening the hood member from the first closed position to the second open position.

7. A system for harvesting a section of a vessel from an incision in a human or animal body comprising:

a light source sized and configured to be inserted into a lumen of the vessel, the light source being sufficient to illuminate substantially the entire vessel section with an intensity which is visible from an exterior of the vessel section;

a viewing element configured to be insertable through the incision and capable of viewing the illuminated vessel section;

at least one tool used to harvest the vessel section, the at least one tool being sized to be inserted through the incision, and a telescoping member having first and second substantially cylindrical segments, the second segment sized to fit within a lumen of the first segment, the telescoping member being adjustable in length from a fully collapsed position to a fully extended position by slidably adjusting the extent to which the second segment is contained in the lumen of the first segment, the telescoping element having a dissecting tool connected thereto.

8. The system of claim 7 wherein the viewing element is connected to the telescoping member.

9. The system of claim 8 further comprising a dissection element connected to the telescoping member.

10. The system of claim 7 further comprising a hood member configured to be moveable from a first closed position to a second open position, the hood member being sized to be inserted through the incision in the closed position and placed adjacent the vessel section, the hood being further configured to create a working space adjacent the vessel when moved to the open position.

11. A system for harvesting a section of a vessel from an incision in a human or animal body comprising:

a light source sized and configured to be inserted into a lumen of the vessel, the light source being sufficient to illuminate substantially the entire vessel section with an intensity which is visible from an exterior of the vessel section;

a viewing element configured to be insertable through the incision and capable of viewing the illuminated vessel section;

at least one tool used to harvest the vessel section, the at least one tool being sized to be inserted through the incision; and a hood member configured to be moveable from a first closed position to a second open position, the hood member being sized to be inserted through the incision in the closed position and placed adjacent the vessel section, the hood being further configured to create a working space adjacent the vessel when moved to the open position.

* * * * *